US010233155B2

(12) United States Patent
Molitor et al.

(10) Patent No.: US 10,233,155 B2
(45) Date of Patent: Mar. 19, 2019

(54) PROCESSES FOR THE PREPARATION OF PESTICIDE COMPOUNDS

(71) Applicant: Dow AgroSciences LLC, Indianapolis, IN (US)

(72) Inventors: Erich J. Molitor, Midland, MI (US); Mark Muehlfeld, Midland, MI (US); Joseck M. Muhuhi, Midland, MI (US); Patrick T. McGough, Midland, MI (US); Gary Roth, Midland, MI (US); David E. Podhorez, Midland, MI (US); Christopher W. Derstine, Midland, MI (US); Stacie L. Santhany, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/853,108

(22) Filed: Dec. 22, 2017

(65) Prior Publication Data
US 2018/0186750 A1 Jul. 5, 2018

Related U.S. Application Data

(60) Provisional application No. 62/440,236, filed on Dec. 29, 2016.

(51) Int. Cl.
C07D 231/38 (2006.01)
(52) U.S. Cl.
CPC ................ C07D 231/38 (2013.01)
(58) Field of Classification Search
None
See application file for complete search history.

(56) References Cited

U.S. PATENT DOCUMENTS

| 3,597,341 | A | 8/1971 | Oswald |
| 4,080,457 | A | 3/1978 | Harrison et al. |
| 4,260,765 | A | 4/1981 | Harrison et al. |
| 4,347,251 | A | 8/1982 | Joseph et al. |
| 4,407,803 | A | 10/1983 | Haviv et al. |
| 4,536,506 | A | 8/1985 | Marcoux et al. |
| 4,556,671 | A | 12/1985 | Copp et al. |
| 4,590,007 | A | 5/1986 | Tucker et al. |
| 4,734,125 | A | 3/1988 | Gehring et al. |
| 4,810,719 | A | 3/1989 | Appleton et al. |
| 4,824,953 | A | 4/1989 | Bronn |
| 5,187,185 | A | 2/1993 | Outcalt et al. |
| 5,220,028 | A | 6/1993 | Iwasawa et al. |
| 5,304,657 | A | 4/1994 | Toki et al. |
| 5,625,074 | A | 4/1997 | Daum et al. |
| 5,631,380 | A | 5/1997 | Haas et al. |
| 5,652,372 | A | 7/1997 | Muller et al. |
| 5,693,657 | A | 12/1997 | Lee et al. |
| 5,726,324 | A | 3/1998 | Huang et al. |
| 5,750,718 | A | 5/1998 | Muller et al. |
| 5,817,677 | A | 10/1998 | Linz et al. |
| 5,854,264 | A | 12/1998 | Anthony et al. |
| 5,854,265 | A | 12/1998 | Anthony et al. |
| 5,869,681 | A | 2/1999 | Muller et al. |
| 6,040,331 | A | 3/2000 | Yamamoto et al. |
| 6,166,243 | A | 12/2000 | Jin et al. |
| 6,218,418 | B1 | 4/2001 | Pevarello et al. |
| 6,258,973 | B1 | 7/2001 | D'Silva et al. |
| 6,348,429 | B1 | 2/2002 | Lim et al. |
| 6,392,081 | B1 | 5/2002 | Ancel et al. |
| 6,410,737 | B1 | 6/2002 | Ancel et al. |
| 6,413,984 | B1 | 7/2002 | Philippo et al. |
| 6,417,187 | B2 | 7/2002 | Hegde et al. |
| 6,506,747 | B1 | 1/2003 | Betageri et al. |
| 6,548,525 | B2 | 4/2003 | Galemmo, Jr. et al. |
| 6,720,427 | B2 | 4/2004 | Sanner et al. |
| 6,878,196 | B2 | 4/2005 | Harada et al. |
| 6,916,927 | B2 | 7/2005 | Bunnage et al. |
| 6,965,032 | B2 | 11/2005 | Freudenberger et al. |
| 7,094,906 | B2 | 8/2006 | Ancel et al. |
| 7,192,906 | B2 | 3/2007 | Hirohara et al. |
| 7,196,104 | B2 | 3/2007 | Askew, Jr. et al. |
| 7,211,270 | B2 | 5/2007 | Lahm et al. |
| 7,319,108 | B2 | 1/2008 | Scwink et al. |
| 7,323,574 | B2 | 1/2008 | Ancel et al. |

(Continued)

FOREIGN PATENT DOCUMENTS

| CN | 87107798 | 5/1988 |
| CN | 1339027 | 3/2002 |

(Continued)

OTHER PUBLICATIONS

Kempe et al., "Responsive Glyco-poly(2-oxaoline)s: Synthesis, Cloud Point Tuning, and Lectin Binding," Biomacromolecules 2011, vol. 12, pp. 2591-2600.
Fields et al., "Preparation of Trifluoromethyl-Pyrazoles and—Pyrazolines by the Reaction of 2,2,2-Trifluorodiazoethane with Carbon-Carbon Multiple Bonds," Journal of Fluorine Chemistry, 1979, vol. 13, pp. 147-158.
Bradbury et al., "Enzyme-catalysed peptide amidation," Eur. J. Biochem. 1987, vol. 169, pp. 579-584.
International Search Report and Written Opinion for PCT/US2014/061005 dated Dec. 16, 2014.
International Search Report and Written Opinion for PCT/US2014/061006 dated Dec. 8, 2014.
International Search Report and Written Opinion for PCT/US2014/061007 dated Dec. 31, 2014.
International Search Report and Written Opinion for PCT/US2014/061009 dated Dec. 8, 2014.

(Continued)

Primary Examiner — Kamal A Saeed
(74) Attorney, Agent, or Firm — Barnes & Thornburg LLP

(57) ABSTRACT

This application relates to efficient and economical synthetic chemical processes for the preparation of pesticidal thioethers. Further, the present application relates to certain novel compounds useful in the preparation of pesticidal thioethers. Specifically, this application relates to a process for the preparation of 3-chloro-1H-pyrazol-4-amine and salts thereof. More particularly, this application relates to a process for the preparation of 3-chloro-1H-pyrazol-4-amine and salts thereof by halogenating and reducing 4-nitropyrazole.

19 Claims, 1 Drawing Sheet

(56) References Cited

U.S. PATENT DOCUMENTS

| | | |
|---|---|---|
| 7,774,978 B2 | 8/2010 | Ding et al. |
| 7,803,832 B2 | 9/2010 | Critcher et al. |
| 7,910,606 B2 | 3/2011 | Nazere et al. |
| 7,923,573 B2 | 4/2011 | Tamaki et al. |
| 8,163,756 B2 | 4/2012 | Flynn et al. |
| 8,222,280 B2 | 7/2012 | Liu et al. |
| 8,815,271 B2 | 8/2014 | Yap et al. |
| 8,901,153 B2 | 12/2014 | Buysse et al. |
| 9,024,031 B1 | 5/2015 | Yang et al. |
| 9,029,554 B1 | 5/2015 | Yang et al. |
| 9,029,555 B1 | 5/2015 | Li et al. |
| 9,029,556 B1 | 5/2015 | Yang et al. |
| 9,044,017 B2 | 6/2015 | Yang et al. |
| 9,085,552 B1 | 7/2015 | Li et al. |
| 9,085,564 B2 | 7/2015 | Yang et al. |
| 9,102,654 B2 | 8/2015 | Yang et al. |
| 9,102,655 B2 | 8/2015 | Yang et al. |
| 9,108,932 B2 | 8/2015 | Ross et al. |
| 9,108,946 B2 | 8/2015 | Yang et al. |
| 9,115,115 B1 | 8/2015 | Yang et al. |
| 9,126,974 B2 | 8/2015 | Yang et al. |
| 9,156,813 B1 | 10/2015 | Li et al. |
| 9,174,962 B2 | 11/2015 | Yang et al. |
| 9,199,942 B2 | 12/2015 | Yang et al. |
| 9,199,964 B1 | 12/2015 | Yang et al. |
| 9,242,987 B2 * | 1/2016 | Ramsden ............ C07D 487/04 |
| 9,249,122 B1 | 2/2016 | Yang et al. |
| 9,255,081 B1 | 2/2016 | Li et al. |
| 9,255,082 B2 | 2/2016 | Yang et al. |
| 9,255,083 B2 | 2/2016 | Yang et al. |
| 9,260,396 B2 | 2/2016 | Yang et al. |
| 9,371,310 B2 | 6/2016 | Yang et al. |
| 9,414,594 B2 | 8/2016 | Yang et al. |
| 9,422,265 B2 | 8/2016 | Li et al. |
| 9,433,215 B2 | 9/2016 | Yang et al. |
| 9,434,712 B2 | 9/2016 | Yang et al. |
| 9,447,048 B2 | 9/2016 | Yang et al. |
| 9,522,900 B2 | 12/2016 | Yang et al. |
| 9,540,342 B2 | 1/2017 | Yang et al. |
| 9,550,751 B2 | 1/2017 | Yang et al. |
| 9,573,931 B2 | 2/2017 | Yang et al. |
| 9,580,403 B2 | 2/2017 | Li et al. |
| 9,580,405 B2 | 2/2017 | Yang et al. |
| 9,604,942 B2 | 3/2017 | Ross et al. |
| 9,611,247 B2 | 4/2017 | Yang et al. |
| 9,661,849 B2 | 5/2017 | Yang et al. |
| 9,663,489 B2 | 5/2017 | Li et al. |
| 9,670,164 B2 | 6/2017 | Yang et al. |
| 9,670,178 B2 | 6/2017 | Yang et al. |
| 9,809,570 B2 | 11/2017 | Yang et al. |
| 9,840,490 B2 | 12/2017 | Li et al. |
| 9,862,702 B2 | 1/2018 | Yang et al. |
| 2002/0013326 A1 | 1/2002 | Tiebes et al. |
| 2003/0153464 A1 | 8/2003 | Nakamura et al. |
| 2003/0213405 A1 | 11/2003 | Harada et al. |
| 2004/0043904 A1 | 3/2004 | Yamaguchi et al. |
| 2004/0082629 A1 | 4/2004 | Iwataki et al. |
| 2004/0255397 A1 | 12/2004 | Fessmann et al. |
| 2005/0009834 A1 | 1/2005 | Itoh et al. |
| 2005/0038059 A1 | 2/2005 | Mueller et al. |
| 2005/0176710 A1 | 8/2005 | Schwink et al. |
| 2006/0135778 A1 | 6/2006 | Schnatterer et al. |
| 2006/0160857 A1 | 7/2006 | Buettelmann et al. |
| 2006/0160875 A1 | 7/2006 | Gaines et al. |
| 2006/0167020 A1 | 7/2006 | Dickerson et al. |
| 2006/0287365 A1 | 12/2006 | Billen et al. |
| 2006/0287541 A1 | 12/2006 | Nishino et al. |
| 2007/0049604 A1 | 3/2007 | Nam et al. |
| 2007/0167426 A1 | 7/2007 | Siddiqui et al. |
| 2007/0259962 A1 | 11/2007 | Deyn et al. |
| 2008/0004301 A1 | 1/2008 | Tamaki et al. |
| 2008/0027046 A1 | 1/2008 | Annan et al. |
| 2008/0199606 A1 | 8/2008 | Karl et al. |
| 2009/0023709 A1 | 1/2009 | Gillespie et al. |
| 2009/0069288 A1 | 3/2009 | Breinlinger et al. |
| 2009/0137524 A1 | 5/2009 | Billen et al. |
| 2009/0275592 A1 | 11/2009 | Zeng et al. |
| 2009/0325956 A1 | 12/2009 | Taniguchi et al. |
| 2010/0130474 A1 | 5/2010 | Bothmann et al. |
| 2010/0204164 A1 | 8/2010 | Crouse et al. |
| 2010/0286169 A1 | 11/2010 | Guiles et al. |
| 2010/0292253 A1 | 11/2010 | Trullinger et al. |
| 2010/0305200 A1 | 12/2010 | Velicelebi et al. |
| 2011/0021771 A1 | 1/2011 | Mallais et al. |
| 2011/0048261 A1 | 3/2011 | Shimura |
| 2011/0098287 A1 | 4/2011 | Bretschneider et al. |
| 2011/0118290 A1 | 5/2011 | Bretschneider et al. |
| 2011/0166129 A1 | 7/2011 | Machacek et al. |
| 2011/0166143 A1 | 7/2011 | Bretschneider et al. |
| 2011/0184188 A1 | 7/2011 | Wade et al. |
| 2011/0201649 A1 | 8/2011 | Matsuzaki et al. |
| 2011/0212949 A1 | 9/2011 | Bretschneider et al. |
| 2011/0275583 A1 | 11/2011 | Bretschneider et al. |
| 2011/0319428 A1 | 12/2011 | Fuβlein et al. |
| 2012/0053146 A1 | 3/2012 | Parker et al. |
| 2012/0053216 A1 | 3/2012 | Creemer et al. |
| 2012/0094837 A1 | 4/2012 | Muhlthau et al. |
| 2012/0095023 A1 | 4/2012 | Bretschneider et al. |
| 2012/0101294 A1 | 4/2012 | Hirota et al. |
| 2012/0110701 A1 | 5/2012 | Garizi et al. |
| 2012/0110702 A1 | 5/2012 | Yap et al. |
| 2012/0115811 A1 | 5/2012 | Du et al. |
| 2012/0165345 A1 | 6/2012 | Bretschneider et al. |
| 2012/0172218 A1 | 7/2012 | Crouse et al. |
| 2012/0220453 A1 | 8/2012 | Lowe et al. |
| 2012/0252770 A1 | 10/2012 | Berger et al. |
| 2012/0252779 A1 | 10/2012 | Ramsden et al. |
| 2013/0019348 A1 | 1/2013 | Crouse et al. |
| 2013/0030190 A1 | 1/2013 | Gharda et al. |
| 2013/0072382 A1 | 3/2013 | Trullinger et al. |
| 2013/0089622 A1 | 4/2013 | Trullinger et al. |
| 2013/0109566 A1 | 5/2013 | Niyaz et al. |
| 2013/0261141 A1 | 10/2013 | Bretschneider et al. |
| 2013/0288893 A1 | 10/2013 | Buysse et al. |
| 2013/0291227 A1 | 10/2013 | Buysse et al. |
| 2013/0324736 A1 | 12/2013 | Ross, Jr. et al. |
| 2013/0324737 A1 | 12/2013 | Ross, Jr. et al. |
| 2013/0338367 A1 | 12/2013 | Numata et al. |
| 2014/0162874 A1 | 6/2014 | Yap et al. |
| 2014/0309446 A1 | 10/2014 | Amajjahe et al. |
| 2015/0112073 A1 | 4/2015 | Yang et al. |
| 2015/0112076 A1 | 4/2015 | Yang et al. |
| 2015/0112078 A1 | 4/2015 | Yang et al. |
| 2015/0112075 A1 | 7/2015 | Yang et al. |
| 2015/0252016 A1 | 9/2015 | Yang et al. |
| 2015/0336929 A1 | 11/2015 | Yang et al. |
| 2016/0031849 A1 | 2/2016 | Yang et al. |
| 2016/0060245 A1 | 3/2016 | Buysse et al. |
| 2016/0075681 A1 | 3/2016 | Li et al. |
| 2016/0152593 A1 | 6/2016 | Li et al. |
| 2016/0152594 A1 | 6/2016 | Yang et al. |
| 2016/0318924 A1 | 11/2016 | Yap et al. |
| 2016/0332987 A1 | 11/2016 | Yang et al. |
| 2016/0345580 A1 | 12/2016 | Yang et al. |
| 2017/0044134 A1 | 2/2017 | Yang et al. |
| 2017/0081288 A1 | 3/2017 | Yang et al. |
| 2017/0101393 A1 | 4/2017 | Li et al. |
| 2017/0215420 A1 | 8/2017 | Yang et al. |
| 2017/0217924 A1 | 8/2017 | Li et al. |
| 2017/0233367 A1 | 8/2017 | Yang et al. |
| 2017/0295786 A1 | 10/2017 | Yang et al. |

FOREIGN PATENT DOCUMENTS

| | | |
|---|---|---|
| CN | 1373662 | 10/2002 |
| CN | 1852885 A | 10/2006 |
| CN | 1307161 C | 3/2007 |
| CN | 101228134 | 7/2008 |
| EP | 0097323 | 1/1984 |
| EP | 0190457 | 8/1986 |
| EP | 0205024 | 12/1986 |
| EP | 0232538 | 8/1987 |
| EP | 0248315 | 12/1987 |
| EP | 0425948 | 5/1991 |

(56) References Cited

FOREIGN PATENT DOCUMENTS

| | | |
|---|---|---|
| EP | 0273549 | 1/1992 |
| EP | 0520274 A2 | 6/1992 |
| EP | 0757987 | 4/1994 |
| EP | 1273582 | 1/2003 |
| EP | 1321463 | 6/2003 |
| EP | 1329160 | 7/2003 |
| EP | 1757590 A1 | 2/2007 |
| JP | 1987-153273 | 7/1987 |
| JP | 1988-174905 | 7/1988 |
| JP | 1989-226815 | 9/1989 |
| JP | 1994/013644 | 6/1994 |
| JP | 1997/036897 | 10/1997 |
| JP | 2003-212864 | 7/2003 |
| JP | 2004-051628 | 2/2004 |
| JP | 2004-292703 | 10/2004 |
| JP | 2006502226 | 1/2006 |
| JP | 2012-188418 | 10/2012 |
| JP | 2013-075871 | 4/2013 |
| JP | 2013-082699 | 5/2013 |
| JP | 2013-082704 | 5/2013 |
| JP | 2013-107867 | 6/2013 |
| JP | 2013-129651 | 7/2013 |
| JP | 2013-129653 | 7/2013 |
| WO | 1998/049166 | 11/1998 |
| WO | 2000/035919 | 6/2000 |
| WO | 2001/12189 | 2/2001 |
| WO | 2001/034127 | 5/2001 |
| WO | 2001/090078 | 11/2001 |
| WO | 2002/083111 | 10/2002 |
| WO | 2003/008405 | 1/2003 |
| WO | 2003/047347 | 6/2003 |
| WO | 2003/072102 | 9/2003 |
| WO | 2004/041813 | 5/2004 |
| WO | 2005/070925 | 8/2005 |
| WO | 2005/074875 | 8/2005 |
| WO | 2006/023462 | 3/2006 |
| WO | 2006/033005 | 3/2006 |
| WO | 2006/046593 | 5/2006 |
| WO | 2006/103045 | 10/2006 |
| WO | 2007/005838 | 1/2007 |
| WO | 2008/090382 | 7/2007 |
| WO | 2007/087427 | 8/2007 |
| WO | 2007/098826 | 9/2007 |
| WO | 2008/005457 | 1/2008 |
| WO | 2008/079277 | 7/2008 |
| WO | 2009/149858 | 12/2009 |
| WO | 2010/006713 | 1/2010 |
| WO | 2010/009290 | 1/2010 |
| WO | 2010/012442 | 2/2010 |
| WO | 2010/033360 | 3/2010 |
| WO | 2010/048207 | 4/2010 |
| WO | 2010/060379 | 6/2010 |
| WO | 2010/075376 | 7/2010 |
| WO | 2010/129497 | 11/2010 |
| WO | 2010/133336 | 11/2010 |
| WO | 2010/146236 | 12/2010 |
| WO | 2011/003065 | 1/2011 |
| WO | 2011/043371 | 4/2011 |
| WO | 2011/045224 | 4/2011 |
| WO | 2011/045240 | 4/2011 |
| WO | 2011/048082 | 4/2011 |
| WO | 2011/091153 | 7/2011 |
| WO | 2011/101229 | 8/2011 |
| WO | 2011/126903 | 10/2011 |
| WO | 2011/128304 | 10/2011 |
| WO | 2011/134964 | 11/2011 |
| WO | 2011/138285 | 11/2011 |
| WO | 2011/163518 | 12/2011 |
| WO | 2012/000896 | 1/2012 |
| WO | 2012/004217 | 1/2012 |
| WO | 2012/007500 | 1/2012 |
| WO | 2012/035011 | 3/2012 |
| WO | 2012/052412 | 4/2012 |
| WO | 2012/061290 | 5/2012 |
| WO | 2012/070114 | 5/2012 |
| WO | 2012/102387 | 8/2012 |
| WO | 2012/108511 | 8/2012 |
| WO | 2012/147107 | 11/2012 |
| WO | 2012/168361 | 12/2012 |
| WO | 2013/000931 | 1/2013 |
| WO | 2013/010946 | 1/2013 |
| WO | 2013/010947 | 1/2013 |
| WO | 2013/062980 | 5/2013 |
| WO | 2013/062981 | 5/2013 |
| WO | 2013/064324 | 5/2013 |
| WO | 2013/156431 | 10/2013 |
| WO | 2013/156433 | 10/2013 |
| WO | 2013/162716 | 10/2013 |
| WO | 2015/058020 | 4/2015 |
| WO | 2015/058022 | 4/2015 |
| WO | 2015/058023 | 4/2015 |
| WO | 2015/058026 | 4/2015 |
| WO | 2015/058028 | 4/2015 |
| WO | 20151058024 | 4/2015 |

OTHER PUBLICATIONS

International Search Report and Written Opinion for PCT/US2014/061010 dated Dec. 15, 2014.
International Search Report and Written Opinion for PCT/US2014/061012 dated Dec. 15, 2014.
International Search Report and Written Opinion for PCT/US2014/061014 dated Dec. 15, 2014.
International Search Report and Written Opinion for PCT/US2014/061016 dated Dec. 15, 2014.
International Search Report and Written Opinion for PCT/US2014/061022 dated Dec. 29, 2014.
International Search Report and Written Opinion for PCT/US2014/061023 dated Dec. 15, 2014.
International Search Report and Written Opinion for PCT/US2014/061024 dated Dec. 15, 2014.
International Search Report and Written Opinion for PCT/US2014/061027 dated Dec. 15, 2014.
International Search Report and Written Opinion for PCT/US2014/061029 dated Dec. 15, 2014.
International Search Report and Written Opinion for PCT/US2014/061030 dated Dec. 15, 2014.
International Search Report and Written Opinion for PCT/US2013/029615 dated May 8, 2013.
Ameduri, B. et al., "Synthesis and polymerization of fluorinated monomers bearing a reactive lateral group Part 4. Preparation of functional perfluorovinyl monomers by radical addition of functional mercaptans to 1,1,2-trifluoro-1,4-pentadiene." J. Fluorine Chemistry, 92, 77-84 (1998).
International Preliminary Report on Patentability for PCT/US2011/058578 dated Dec. 21, 2012.
International Search Report and Written Opinion for PCT/US2011/058578 dated Apr. 5, 2012.
Kadam, S.S. et al., "Synthesis and Tautomerism of Substituted Pyrazolo[4,3-c]pyrazoles." Eur. J. Chem., 6811-6822 (2013).
Gorelik; Zhumai Organicheskol khimi, 1980 (16), 1322, Abstract, Chemical Abstracts, Accession No. 1980;620652.
National Center for Biotechnology Information, PubChem Compound Database; CID=17132489,https://pubchem.ncbi.nlm.nih.gov/compound/17132489, create date Nov. 13, 2007.
Frigola; European Journal of Medicinal Chemistry 1989, 435-445.
Binz et al. "Derivatives of pyridine, etc.," CA 25:30083 (1931).
Lahm, G. et al., "Rynaxypyr: A new insecticidal anthranilic diamide that acts as a potent and selective ryanodine receptor activator," Bioorganic and Medical Chemistry Letters, 2007, 17, 6274-6279.
Giornal, F. et al., "A New Synthesis and Process Development of Bis(fluoroalkyl)pyrazoles as Novel Agrophores," Organic Process Research and Development, 2014, 18, 1002-1009.
Lieser, T. et al., "Artificial organic high polymers, VII, New acrylyl derivatives and their polymerization products," Chemische Berichte, VCH, DE, 1951, 84, 4-12.
Tanaka, N. et al., "Synthesis of pyrazole carboxylic acid via cobalt-catalyzed phase oxidation," Chemistry Letters, Chemical Society of Japan, 1991, 4, 585-588.

(56) References Cited

OTHER PUBLICATIONS

Ross, John R. et al. "Synthesis of 7-Substituted 5,6-Dimethyl-2,4-dioxo-1,2,4,7-tetrahydropyrrolo[2,3-d][1,3]oxazines", Synthesis, v. 1985, No. 8, Jan. 1, 1985, pp. 796-798.
Chan et al., "Nucleophile-Initiated Thiol-Michael Reactions: Effect of Organocatalyst, Thiol, and Ene", Macromolecules, 2010, vol. 43 (15), pp. 6381-6388; DOI: 10.1021/ma101069c abstract; p. 6382, col. 1, para 4; p. 6385, Scheme 1; p. 6386, Fig 6; Fig 8; Fig 9.
Mutsumi Sato et al., "2, 2'—Azobis (2,4-dimethyl-4-methoxy) valeronitrile (V-70)" J. Synth. Org. Chem. JPn, 2006, vol. 64, No. 4, pp. 420-422.
International Search Report and Written Opinion for PCT/US2017/068253 dated May 23, 2018.

\* cited by examiner

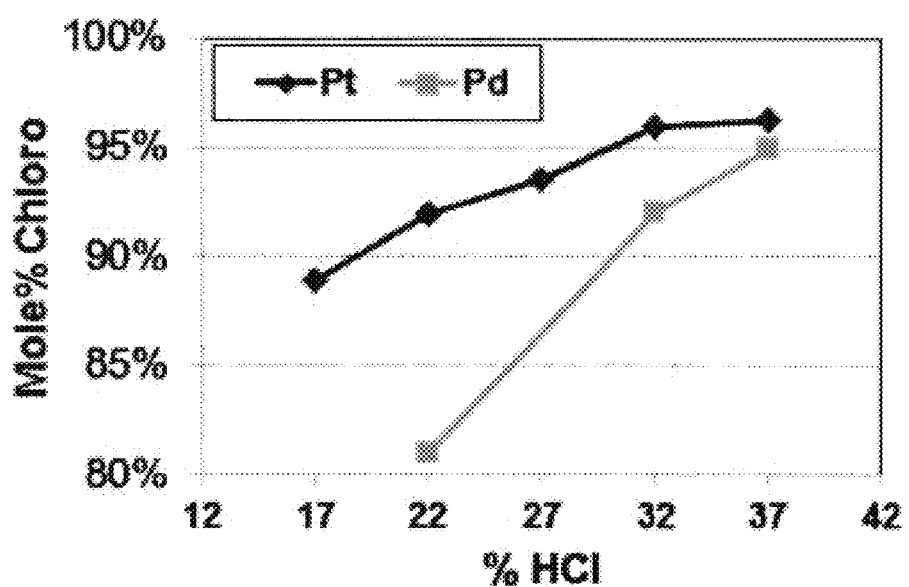

PROCESSES FOR THE PREPARATION OF PESTICIDE COMPOUNDS

CROSS-REFERENCE TO RELATED APPLICATIONS

This application claims priority under 35 U.S.C. § 119(e) to U.S. Provisional Application Ser. No. 62/440,236 filed Dec. 29, 2016, which is incorporated herein by this reference in its entirety.

TECHNICAL FIELD OF THE DISCLOSURE

This application relates to efficient and economical synthetic chemical processes for the preparation of pesticidal thioethers. Further, the present application relates to certain novel compounds useful in the preparation of pesticidal thioethers. Specifically, this application relates to a process for the preparation of 3-chloro-1H-pyrazol-4-amine and salts thereof. More particularly, this application relates to a process for the preparation of 3-chloro-1H-pyrazol-4-amine and salts thereof by halogenating and reducing 4-nitropyrazole.

BACKGROUND OF THE DISCLOSURE

The following process is disclosed by Dahlbom, R. et al. *Acta Pharm. Suec.* 22, 147-156(1985).

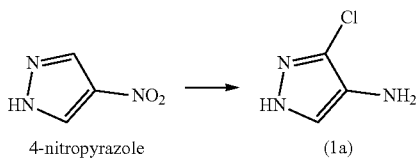 [SMILES: O=[N+]([O-])c1cn[nH]c1 ; Nc1c[nH]nc1Cl]

Dahlbom et al. disclose on page 151 (paragraph 4) that "4-[n]itropyrazole (3.0 g, 0.027 mol) in ethanol (50 ml) and 5M HCl (12 ml) was hydrogenated over a palladium catalyst (5% on $Al_2O_3$) in a Parr apparatus at an initial pressure of 3-3.5 atm for 2 h. After filtration and evaporation of the solvent in vacuo, the residue was purified by column chromatography ($Al_2O_3$, $CHCl_3$—$CH_3OH$ (9:1)), affording 2.1 g (68%) of the title compound[.]"

For purposes of clarity, 5M (mol/L) HCl (hydrochloric acid), is a concentration of about 15% by weight hydrogen chloride gas in water. Additionally, 3-3.5 atm (atmospheres), is a pressure of about 300 kilopascals (kPa) to about 350 kPa.

It is noteworthy that the process disclosed by Dahlbom et al. was performed at a volume/volume (v/v) ratio of ethanol to hydrochloric acid of about 4:1. Likewise, the Dahlbom report does not disclose the temperature at which this process is conducted, nor does it report the catalyst loading of palladium on alumina.

The following process is disclosed by Ramsden, N. et al. WO 2011/048082 A1, 115(2011).

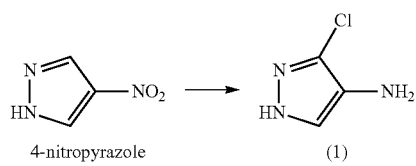

Ramsden et al. disclose on page 115 (lines 5-9) that "[a] solution of 4-nitropyrazole (500 mg, 4.4 mmol) and palladium on alumina (50 mg) in ethanol (10 mL) and hydrochloric acid (2 mL, 6M aqueous solution) was stirred at rt under a balloon of $H_2$ for 16 h. The mixture was then filtered through Celite and the filtrate concentrated in vacuo to give 3-chloro-1H-pyrazol-4-amine."

For purposes of clarity, 6M hydrochloric acid, is a concentration of about 19% by weight hydrogen chloride gas in water. Additionally, a balloon of $H_2$ (hydrogen gas), is a pressure of about 1 atmosphere, which is equivalent to a pressure of about 100 kPa.

It is noteworthy that the process disclosed by Ramsden et al. was performed at a volume/volume (v/v) ratio of ethanol to hydrochloric acid of 5:1. Likewise, the Ramsden report does not disclose the weight percentage of palladium on alumina, the type of reaction vessel used, or the yield of the reaction.

BRIEF DESCRIPTION OF THE DRAWINGS

FIG. 1 shows a comparison of selectivity with Pt/C vs Pd/Alumina catalysts at different HCl concentrations.

DETAILED DESCRIPTION OF THE DISCLOSURE

This application relates to efficient and economical synthetic chemical processes for the preparation of pesticidal thioethers. Further, the present application relates to certain novel compounds useful in the preparation of pesticidal thioethers. Specifically, this application relates to a process for the preparation of 3-chloro-1H-pyrazol-4-amine and salts thereof. More particularly, this application relates to a process for the preparation of 3-chloro-1H-pyrazol-4-amine and salts thereof by halogenating and reducing 4-nitropyrazole. The process of the present application is described in Scheme 1 below.

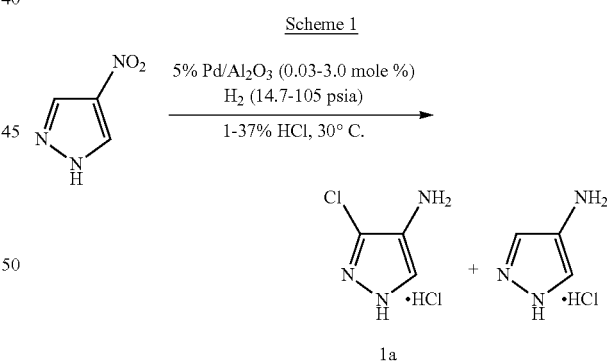

In Scheme 1, 3-chloro-1H-pyrazol-4-amine hydrochloride (1a) can be prepared by halogenating and reducing 4-nitropyrazole. In the process of Scheme 1, the halogenation occurs in the presence of from about 1% to about 40% HCl. In some embodiments, the HCl concentration can be from about 31% (about 10 M) to about 38% (about 12.4 M). In some embodiments, the HCl concentration is about 37% (about 12 M). It has been discovered that the halogenation occurs at the 3-carbon of 4-nitropyrazole in the presence of higher concentrations of HCl, such as about 31% (about 10 M) to about 38% (about 12.4 M), such as about 37% (about 12 M).

The process of Scheme 1 can be conducted in the presence of an optional alcoholic solvent, such as ethanol or isopropanol, at a v/v ratio of alcoholic solvent to hydrochloric acid of about 1:99 to about 3:4, preferably about 1:9 to about 3:4, more preferably about 1:9.

It was surprisingly discovered, that use of about 31% to about 38% hydrochloric acid, optionally in the presence of an additional alcoholic solvent at a v/v ratio of alcoholic solvent to hydrochloric acid of about 1:9 to about 3:4, provides a selectivity of the desired halogenated product 3-chloro-1H-pyrazol-4-amine hydrochloride (1a) to the undesired non-halogenated by-product 1H-pyrazol-4-amine hydrochloride of about 7:1 to about 49:1.

It was surprisingly discovered, that use of about 37% hydrochloric acid, optionally in the presence of isopropanol at a v/v ratio of isopropanol to hydrochloric acid of about 1:9, provides a selectivity of the desired halogenated product 3-chloro-1H-pyrazol-4-amine hydrochloride (1a) to the undesired product 1H-pyrazol-4-amine hydrochloride of about 16:1 to about 49:1.

In the process of Scheme 1, the reduction can be carried out in the presence of hydrogen gas at a pressure of about 100 kPa (about 14.5 psia) to about 30,000 kPa (about 4350 psia). In some embodiments, the pressure is from about 100 kPa (about 14.5 psia) to about 6,000 kPa (about 870 psia). In some embodiments, the pressure is from about 100 kPa (about 14.5 psia) to about 800 kPa (about 116 psia).

The reduction can be catalyzed by a transition metal catalyst, such as palladium on alumina (Pd/Al$_2$O$_3$), which has a metal to solid support weight percentage of about 1 weight percent to about 10 weight percent, more preferably about 5 weight percent. A catalyst loading of about 0.003 mol percent to about 3 mol percent of the transition metal catalyst to 4-nitropyrazole is preferred for the reduction.

The process of halogenating and reducing 4-nitropyrazole to 3-chloro-1H-pyrazol-4-amine hydrochloride (1a) shown in Scheme 1 can be conducted at temperatures of about 20° C. to about 60° C., preferably about 30° C. to about 40° C. In some embodiments, the reaction can be carried out in a glass reactor or a glass-lined Hastelloy C pressure reactor.

In Scheme 2, 3-chloro-1H-pyrazol-4-amine (1) is prepared by free-basing 3-chloro-1H-pyrazol-4-amine hydrochloride (1a) with a base, such as sodium bicarbonate or triethylamine.

Scheme 2

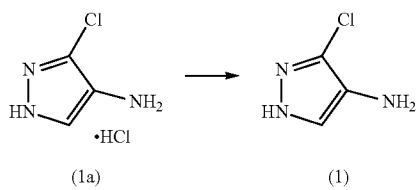

(1a)     (1)

In an alternative embodiment, the compound of the formula 1a can be prepared according to Scheme 3.

Scheme 3

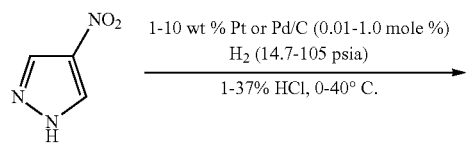

1-10 wt % Pt or Pd/C (0.01-1.0 mole %)
H$_2$ (14.7-105 psia)
1-37% HCl, 0-40° C.

-continued

1a

In the process of Scheme 3, 4-nitropyrazole is treated under reductive chlorination conditions, wherein the reductive chlorination conditions comprise about 1 to about 10 wt % Pt or Pd/C, or a mixture thereof, in the presence of aqueous HCl under a hydrogen atmosphere of from about 14 to about 105 psia. The reductive chlorination reaction of 4-nitropyrazole to provide 3-chloro-1H-pyrazol-4-amine was previously described using Pd/Al$_2$O$_3$ as the catalyst gave a low yield (58%) and did not mention the formation of any other impurities. The process of Scheme 3 affords high selectivity (>95%) of 3-chloro-1H-pyrazol-4-amine hydrochloride while using concentrations of HCl lower than 37%. The catalyst used for this process can be platinum or palladium on carbon (Pt/C or Pd/C), or a mixture thereof. Relative to Pd/Al$_2$O$_3$ catalyst, Pd/C or Pt/C can provide higher selectivity at a given HCl concentration. The selectivity benefit with Pt/C is more pronounced at lower HCl concentrations. Without being bound by theory, it is believe that the activity of Pt/C catalyst is better, which allows the reaction to proceed to completion more quickly, or with a lower amount of catalyst. Furthermore, it has been discovered that the Pt/C or Pd/C catalyst solves the problem of a difficult catalyst filtration which was observed with the Pd/Al$_2$O$_3$ catalyst, as the filtration of Pt/C or Pd/C catalyst is fast. In addition, problems encountered in downstream steps that may be attributed to the presence of minute quantities of aluminum salts dissolved in the reaction product mixture are eliminated by using the Pt/C or Pd/C catalyst. In some embodiments, the reaction can be carried out in a glass reactor or a glass-lined Hastelloy C pressure reactor.

It will be appreciated that the reduction step of the processes described herein can be carried out in the presence of additional palladium catalysts, such as palladium(II) acetate, palladium(II) chloride, palladium(II) bromide, palladium(II) iodide, palladium(II) acetylacetonate, allylpalladium(II) chloride dimer, palladium(II) nitrate hydrate, palladium(II) sulfate, palladium on carbon, palladium on silica, palladium on calcium carbonate, palladium on strontium carbonate, palladium on barium sulfate, palladium on barium sulfate, and palladium on activated charcoal.

It will be appreciated that the reduction step of the processes described herein can be carried out in the presence of additional platinum catalysts, such as (2,2'-bipyridine)dichloroplatinum(II), cis-bis(acetonitrile)dichloroplatinum(II), cis-bis(benzonitrile)dichloroplatinum(II), bis(tri-tert-butylphosphine)platinum(0), chloroplatinic acid hydrate, (1,5-cyclooctadiene)dimethylplatinum(II), platinum(II) chloride, platinum(II) bromide, platinum(II) iodide, platinum(IV) oxide, platinum on alumina, platinum on silica, sulfided platinum on carbon, and platinum on activated charcoal.

It will be appreciated that the reduction step of the processes described herein can be carried out in the presence of other transition metals, such as iron, nickel, tin, and catalysts or pre-catalysts that may be prepared from them.

For small scale, bench top applications, the processes described herein can be conducted in an autoclave reactor, a glass reactor, or a glass-lined reactor, preferably a glass reactor or a glass-lined reactor. For large, commercial scale applications, the processes described herein can be conducted in glass-lined reactors with a total capacity of about 50 L (about 13 gallons) to about 95,000 L (about 25,000 gallons), preferably about 3700 L (about 970 gallons) to about 38,000 L (about 10,000 gallons).

The processes disclosed herein can be described according to any of the following numbered embodiments.

1. A process for the preparation of 3-chloro-1H-pyrazol-4-amine hydrochloride (1a)

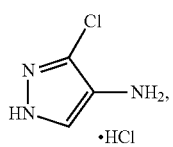

which comprises halogenating and reducing 4-nitropyrazole

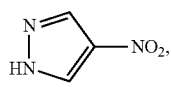

with
(a) about 15% to about 40% hydrochloric acid,
(b) hydrogen gas at pressures of about 100 kPa to about 800 kPa, and
(c) a transition metal catalyst,
at temperatures of about 20° C. to about 60° C., optionally in the presence of an additional alcoholic solvent at a v/v ratio of alcoholic solvent to hydrochloric acid of about 1:99 to about 3:4.

2. A process according to 1, wherein 4-nitropyrazole

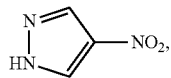

is halogenated and reduced with
(a) about 36% to about 38% hydrochloric acid,
(b) hydrogen gas at pressures of about 100 kPa to about 800 kPa, and
(c) palladium on alumina,
at temperatures of about 30° C. to about 40° C., optionally in the presence of an additional alcoholic solvent at a v/v ratio of alcoholic solvent to hydrochloric acid of about 1:99 to about 3:4.

3. A process according to 1, wherein 4-nitropyrazole

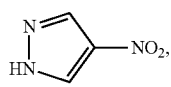

is halogenated and reduced with
(a) about 36% to about 38% hydrochloric acid,
(b) hydrogen gas at pressures of about 100 kPa to about 800 kPa, and
(c) platinum on carbon, at temperatures of about 30° C. to about 40° C., optionally in the presence of an additional alcoholic solvent at a v/v ratio of alcoholic solvent to hydrochloric acid of about 1:99 to about 3:4.

4. A process according to 1 or 2, wherein 4-nitropyrazole

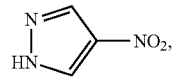

is halogenated and reduced with
(a) about 36% to about 38% hydrochloric acid,
(b) hydrogen gas at pressures of about 100 kPa to about 800 kPa, and
(c) palladium on alumina,
at temperatures of about 30° C. to about 40° C., optionally in the presence of an additional alcoholic solvent at a v/v ratio of alcoholic solvent to hydrochloric acid of about 1:9 to about 3:4.

5. A process according to 1 or 2, wherein 4-nitropyrazole

is halogenated and reduced with
(a) about 36% to about 38% hydrochloric acid,
(b) hydrogen gas at pressures of about 100 kPa to about 800 kPa, and
(c) palladium on alumina,
at temperatures of about 30° C. to about 40° C., optionally in the presence of an additional alcoholic solvent at a v/v ratio of alcoholic solvent to hydrochloric acid of about 1:9.

6. A process according to 1 or 3, wherein 4-nitropyrazole

is halogenated and reduced with
(a) about 36% to about 38% hydrochloric acid,
(b) hydrogen gas at pressures of about 100 kPa to about 800 kPa, and
(c) platinum on carbon,
at temperatures of about 30° C. to about 40° C., optionally in the presence of an additional alcoholic solvent at a v/v ratio of alcoholic solvent to hydrochloric acid of about 1:9 to about 3:4.

7. A process according to 1 or 3, wherein 4-nitropyrazole

is halogenated and reduced with
(a) about 36% to about 38% hydrochloric acid,
(b) hydrogen gas at pressures of about 100 kPa to about 800 kPa, and
(c) platinum on carbon, at temperatures of about 30° C. to about 40° C., optionally in the presence of an additional alcoholic solvent at a v/v ratio of alcoholic solvent to hydrochloric acid of about 1:9.

8. A process for the preparation of 3-chloro-1H-pyrazol-4-amine hydrochloride (1a)

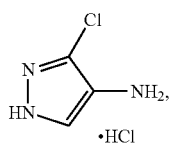
(1a)

which comprises halogenating and reducing 4-nitropyrazole

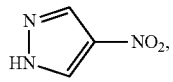

with
(a) about 10 M to about 13 M hydrochloric acid,
(b) hydrogen gas at pressures of about 100 kPa to about 800 kPa, and
(c) a transition metal catalyst,
at temperatures of about 20° C. to about 60° C., optionally in the presence of an additional alcoholic solvent at a v/v ratio of alcoholic solvent to hydrochloric acid of about 1:99 to about 3:4.

9. A process according to 8, wherein 4-nitropyrazole

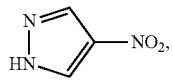

is halogenated and reduced with
(a) about 11.6 M to about 12.4 M hydrochloric acid,
(b) hydrogen gas at pressures of about 100 kPa to about 800 kPa, and
(c) palladium on alumina,
at temperatures of about 30° C. to about 40° C., optionally in the presence of an additional alcoholic solvent at a v/v ratio of alcoholic solvent to hydrochloric acid of about 1:99 to about 3:4.

10. A process according to 8, wherein 4-nitropyrazole

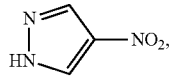

is halogenated and reduced with
(a) about 11.6 M to about 12.4 M hydrochloric acid,
(b) hydrogen gas at pressures of about 100 kPa to about 800 kPa, and
(c) platinum on carbon,
at temperatures of about 30° C. to about 40° C., optionally in the presence of an additional alcoholic solvent at a v/v ratio of alcoholic solvent to hydrochloric acid of about 1:99 to about 3:4.

11. A process according to 8 or 9, wherein 4-nitropyrazole

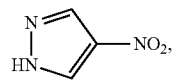

is halogenated and reduced with
(a) about 11.6 M to about 12.4 M hydrochloric acid,
(b) hydrogen gas at pressures of about 100 kPa to about 800 kPa, and
(c) palladium on alumina,
at temperatures of about 30° C. to about 40° C., optionally in the presence of an additional alcoholic solvent at a v/v ratio of alcoholic solvent to hydrochloric acid of about 1:9 to about 3:4.

12. A process according to 8 or 9, wherein 4-nitropyrazole

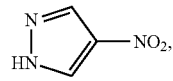

is halogenated and reduced with
(a) about 11.6 M to about 12.4 M hydrochloric acid,
(b) hydrogen gas at pressures of about 100 kPa to about 800 kPa, and
(c) palladium on alumina,
at temperatures of about 30° C. to about 40° C., optionally in the presence of an additional alcoholic solvent at a v/v ratio of alcoholic solvent to hydrochloric acid of about 1:9.

13. A process according to 8 or 10, wherein 4-nitropyrazole

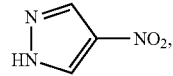

is halogenated and reduced with
(a) about 11.6 M to about 12.4 M hydrochloric acid,
(b) hydrogen gas at pressures of about 100 kPa to about 800 kPa, and
(c) platinum on carbon,
at temperatures of about 30° C. to about 40° C., optionally in the presence of an additional alcoholic solvent at a v/v ratio of alcoholic solvent to hydrochloric acid of about 1:9 to about 3:4.

14. A process according to 8 or 10, wherein 4-nitropyrazole

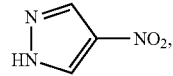

is halogenated and reduced with
(a) about 11.6 M to about 12.4 M hydrochloric acid,
(b) hydrogen gas at pressures of about 100 kPa to about 800 kPa, and
(c) platinum on carbon,
at temperatures of about 30° C. to about 40° C., optionally in the presence of an additional alcoholic solvent at a v/v ratio of alcoholic solvent to hydrochloric acid of about 1:9.

15. A process according to any one of 1 to 14 further comprising, free-basing 3-chloro-1H-pyrazol-4-amine hydrochloride (1a)

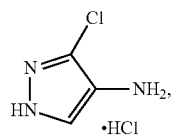

(1a)

with a base to yield 3-chloro-1H-pyrazol-4-amine (1)

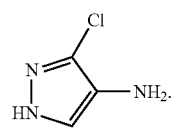

(1)

16. A process according to any one of 2, 4, 5, 9, 11, or 12, wherein palladium on alumina has a metal to solid support weight percentage of about 1 weight percent to about 10 weight percent.

17. A process according to any one of 2, 4, 5, 9, 11, or 12, wherein palladium on alumina has a metal to solid support weight percentage of 5 weight percent.

18. A process according to any one of 3, 6, 7, 10, 13, or 14, wherein platinum on carbon has a metal to solid support weight percentage of about 1 weight percent to about 10 weight percent.

19. A process according to any one of 3, 6, 7, 10, 13, or 14, wherein platinum on carbon has a metal to solid support weight percentage of 5 weight percent.

20. A process according to any one of 1 to 14, wherein the alcoholic solvent is ethanol.

21. A process according to any one of 1 to 14, wherein the alcoholic solvent is isopropanol.

EXAMPLES

These examples are for illustration purposes and are not to be construed as limiting this disclosure to only the embodiments disclosed in these examples.

Starting materials, reagents, and solvents that were obtained from commercial sources were used without further purification. Melting points are uncorrected. Examples using "room temperature" were conducted in climate controlled laboratories with temperatures ranging from about 20° C. to about 24° C. Molecules are given their known names, named according to naming programs within Accelrys Draw, ChemDraw, or ACD Name Pro. If such programs are unable to name a molecule, such molecule is named using conventional naming rules. $^1$H NMR spectral data are in ppm ($\delta$) and were recorded at 300, 400, 500, or 600 MHz; $^{13}$C NMR spectral data are in ppm ($\delta$) and were recorded at 75, 100, or 150 MHz, and $^{19}$F NMR spectral data are in ppm ($\delta$) and were recorded at 376 MHz, unless otherwise stated.

Example 1

Preparation of 3-chloro-1H-pyrazol-4-amine Hydrochloride, Compound 1a, Using Pd/Al$_2$O$_3$ Catalyst

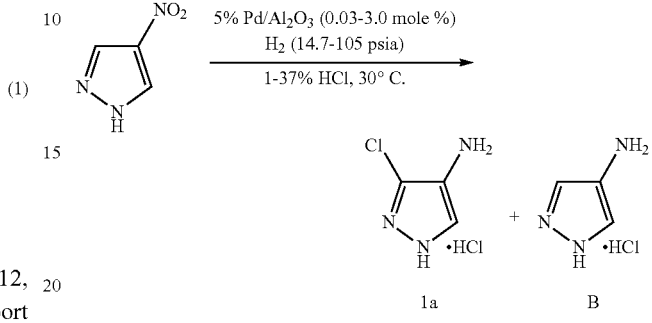

1A. General Method for the Preparation of 3-chloro-1H-pyrazol-4-amine Hydrochloride, Compound 1a Using High Pressure Glass Lined Hastelloy Reactor To a Hastelloy C autoclave reactor was added 4-nitropyrazole (4.50 g, 39.8 mmol), EtOH (45 mL), 37% HCl (60 mL), and 5% Pd/Al$_2$O$_3$ (240 mg, 0.11 mmol). The reactor was assembled and stirred under a N$_2$ atmosphere. The reaction temperature was adjusted to 30° C., and the mixture was sparged with N$_2$ (2 times) and then checked for pressure leaks using N$_2$. The reaction was then purged with H$_2$ (144 psig) to remove any left over N$_2$, and then vented. H$_2$ was then added to a pressure of 104 psig and reaction let stir at that pressure. Upon determination of reaction completeness the reaction was purged with N$_2$ (2times) and disassembled. The crude solution was then filtered using a glass fiber filter and assayed using an internal method. The ratio of the products 1a to B were then determined using 1H NMR based on known literature spectra.

1B. General Method for the Preparation of 3-chloro-1H-pyrazol-4-amine Hydrochloride, Compound 1a Using Glass Reactor To a 4 L glass reactor was added 4-nitropyrazole (76.3 g, 0.66 mol, 98.3% assay), 5% Pd/Al$_2$O$_3$ (44.4 g, 19.9 mmol, 4.53% water wet), and 37% aq, hydrochloric acid 1035 g. The reactor temperature was adjusted to 30° C. The reactor headspace was purged with N$_2$, then H$_2$ (without agitation). The agitation blade speed was set to 300 RPM, and then H$_2$ was bubbled through the reactor at a low flow rate (<100 mL/min). Upon determination of reaction completion, the reaction was purged with N$_2$, and the catalyst was filtered using a glass fiber filter and assayed using an internal method. The ratio of the products 1a and B were then determined using 1H NMR based on known literature spectra.

Table 1 provides a summary of conditions and results for preparing using the above procedures 1A and 1B where the ratio of the products 1a to B was determined by 1H NMR based on known literature spectra.

TABLE 1

| Entry | Method | Solvent (v/v ratio) | H₂ (psia) | Temp (C.) | 1a Yield (in-pot) | 1a:B (molar) |
|---|---|---|---|---|---|---|
| 1 | 1A | EtOH/6M HCl (5:2) | 105 | 30 | 59 | 76:24 |
| 2 | 1A | EtOH/6M HCl (2:3) | 105 | 30 | 69 | 84:16 |
| 3 | 1A | EtOH/6M HCl (3:4) | 105 | 30 | 68 | 87:13 |
| 4 | 1A | EtOH/10.2M HCl (1:6) | 105 | 30 | — | 89:11 |
| 5 | 1A | EtOH/12M HCl (3:4) | 15 | 30 | 77 | 91:9 |
| 6 | 1A | EtOH/9M HCl (3:4) | 15 | 30 | 74 | 86:14 |
| 7 | 1B | 5.7M HCl | 15 | 30 | 81 | 81:19 |
| 8 | 1B | 10.2M HCl | 15 | 30 | 87 | 92:8 |
| 9 | 1B | 12M HCl | 15 | 30 | 94 | 94:6 |
| 10 | 1B | 12M HCl | 15 | 30 | 96 | 97:3 |
| 11 | 1B | 12M HCl | 15 | 40 | 95 | 98:2 |
| 12 | 1B | 12M HCl | 35 | 30 | — | 97:2 |

Example 2

Preparation of 3-chloro-1H-pyrazol-4-amine Hydrochloride, Compound 1a, Using Pt/C or a Mixture of Pt/C and Pd/C Catalyst

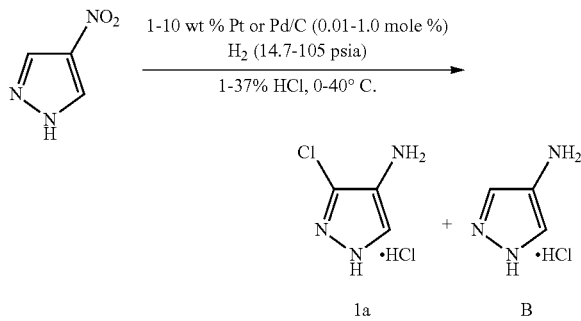

2A. General Method for the Preparation of 3-chloro-1H-pyrazol-4-amine Hydrochloride, Compound 1a Using High Pressure Glass Lined Hastelloy Reactor In a glass lined Hastelloy C Parr reactor was added 4-nitropyrazole (7.17 g, 97.6% purity, 61.9 mmol), 37% HCl (73.5 mL, 86.97 g), 2-propanol (IPA, 8.15 mL, 6.3 g, 10 volume %), and 5% Pt/C catalyst (1.35 g, 4.86 wt % Pt, 0.54 mole % Pt relative to 4-nitropyrazole). The reactor was sealed and the vessel was inerted by pressurizing with nitrogen (150 psig) and venting (2 times) and then checked for leaks using nitrogen pressure at 150 psig. The vessel was vented and then purged with hydrogen (100 psig) and then pressurized to 90 psig hydrogen. The reaction was heated to 30° C. and the agitation was set to 800 rpm. The hydrogen uptake rate was monitored and the reaction was continued until the hydrogen uptake rate reached 0 after 2.5 hours. The reaction was cooled, and the vessel was purged with nitrogen (2 times). The reactor was opened and the product mixture was collected. The reaction mixture was assayed using an internal standard HPLC method to determine a reaction yield of 96.8% of 3-chloro-1H-pyrazol-4-amine hydrochloride (1a). The ratio of the products 1a to B were then determined using 1H NMR based on known literature spectra.

2B. General Method for the Preparation of 3-chloro-1H-pyrazol-4-amine Hydrochloride, Compound 1a Using Glass Reactor To a 4 L glass jacketed reactor was added 6.26 g of water wet 5% Pt/C catalyst (58.5% water, 2.08% Pt when corrected for water, 0.1 mole %), 37% HCl (930.6 g), 4-nitropyrazole (77.0 g, 97.6 wt % purity, 0.66 mole), and isopropanol (70.26 g). The mixture was agitated at 400 rpm and warmed to 30° C. The reactor headspace was purged with nitrogen and then hydrogen (without agitation). The agitation was set to 300 rpm, and then hydrogen was bubbled subsurface through the reaction mixture at 0.2 L/min After 24 hours of reaction time, the reaction was incomplete at approximately 50% conversion. The reaction was purged with nitrogen and additional 5% Pt/C catalyst (6.23 g) was added to the reaction. Hydrogen addition was resumed and 100% conversion was attained after 5 additional hours of reaction time. The reaction mixture was purged with nitrogen and the catalyst was removed by filtration through a glass fiber filter. The filtered product mixture was assay by an internal standard HPLC method to determine an in-pot yield of 93.5% of 3-chloro-1H-pyrazol-4-amine hydrochloride (1a). The ratio of the products 1a to B were then determined using 1H NMR based on known literature spectra.

Table 2 provides a summary of conditions and results for preparing using the above procedures 2A and 2B where the mole % of product 1a was determined by 1H NMR as the ratio of the products 1a to B based on known literature spectra. FIG. 1 provides a Comparison of selectivity with Pt/C vs Pd/Alumina catalysts at different HCl concentrations. In the column "Type" this indicates the manufacturer for: A is Evonik Industries Noblyst® P2060; B is Evonik Industries Noblyst® P2061; C is Johnson Matthey B1034018-5; D is Sigma Aldrich lot MKBT9539V; E is Evonik Industries Noblyst® P2055; and F is Clariant lot 136-63.

TABLE 2

| Catalyst | Type | Catalyst load (mole %) | wt % HCl | vol % IPA solvent | Temp (° C.) | Pressure (psig) | In Pot yield (%) | 1a (mole %) |
|---|---|---|---|---|---|---|---|---|
| 5% Pt/C | A | 0.50% | 37 | 10% | 30 | 90 | 94.5 | 95 0 |
| 1% Pt/C, 4% Pd/C | | 0 50% | 37 | 10% | 30 | 90 | 89.3 | 90 5 |
| 5% Pt/C | B | 0.50% | 37 | 10% | 30 | 90 | 93.9 | 93 2 |
| 5% Pt/C | C | 0.50% | 37 | 10% | 30 | 90 | 96.0 | 95.9 |
| 1% Pt/C | | 0 50% | 37 | 10% | 30 | 90 | 65.0 | 63.0 |
| 5% Pt/C | D | 0.50% | 37 | 10% | 30 | 90 | 96.8 | 96 3 |
| 5% Pt/C | A | 0.50% | 37 | 0 | 30 | 90 | 92.5 | 95.9 |
| 5% Pt/C | A | 0.10% | 37 | 10% | 30 | 90 | 91.9 | 96 9 |

TABLE 2-continued

| Catalyst | Catalyst Type | Catalyst load (mole %) | wt % HCl | vol % IPA solvent | Temp (° C.) | Pressure (psig) | In Pot yield (%) | 1a (mole %) |
|---|---|---|---|---|---|---|---|---|
| 5% Pt/C | A | 0.50% | 37 | 10% | 30 | 90 | 95.2 | 96.5 |
| 5% Pt/C | B | 0.50% | 37 | 0 | 30 | 90 | 88.5 | 93.4 |
| 5% Pt/C | B | 0 10% | 37 | 10% | 30 | 90 | 94.7 | 95 6 |
| 5% Pt/C | A | 0.10% | 32 | 0 | 30 | 90 | 96.6 | 96 0 |
| 5% Pt/C | A | 0 10% | 37 | 0 | 30 | 90 | 95.2 | 96 2 |
| 5% Pt/C | A | 0 10% | 22 | 0 | 30 | 90 | 87.0 | 91.9 |
| 5% Pt/C | A | 0.10% | 27 | 0 | 30 | 90 | 91.5 | 93.5 |
| 5% Pt/C | A | 0.10% | 17 | 0 | 30 | 90 | 83.2 | 88.9 |
| PtCl₂ | | 0 50% | 37 | 10% | 30 | 90 | 14.0 | 78 0 |
| 5% Pt/C | E | 0.10% | 22 | 0 | 30 | 90 | 90.9 | 92 6 |
| 3% Pt/C | | 0.10% | 22 | 0 | 30 | 90 | 88.0 | 88.7 |
| 5% Pt/C | A | 0.10% | 37 | 10% | 0-5 | 90 | 95.3 | 97.7 |
| 5% Pt/C | A | 0.10% | 32 | 0 | 30 | 70 | 91.2 | 97.0 |
| 5% Pt/C | A | 0 10% | 32 | 0 | 40 | 90 | 95.4 | 97 0 |
| 5% Pt/C | A | 0 10% | 22 | 0 | 30 | 70 | 88.3 | 90.3 |
| 5% Pt/C | A | 0.10% | 37 | 10% | 20 | 90 | 99 0 | 96.1 |
| 5% Pt/C | B | 0 10% | 32 | 0 | 30 | 90 | 96.0 | 94 2 |
| 5% Pt/C | B | 0 10% | 37 | 0 | 30 | 90 | 94.6 | 95 7 |
| 5% Pt/C | F | 0.10% | 32 | 0 | 30 | 90 | 94.7 | 93.3 |
| 5% Pt/C | E | 0.10% | 32 | 0 | 30 | 90 | 90.7 | 92.9 |
| 5% Pt/C | E | 010% | 32 | 0 | 30 | 90 | 90 0 | 92 8 |
| 5% Pt/C | A | 0.05% | 32 | 0 | 30 | 90 | 98.5 | 95.3 |
| 10% Pt/C | E | 0 10% | 22 | 0 | 30 | 90 | 87.8 | 90.0 |
| 10% Pt/C | A | 0.10% | 22 | 0 | 30 | 90 | 87.8 | 89 3 |
| 10% Pt/C | E | 0.05% | 22 | 0 | 30 | 90 | 89.6 | 89 8 |
| 10% Pt/C | A | 0.05% | 22 | 0 | 30 | 90 | 90.2 | 89.7 |
| 10% Pt/C | E | 0.05% | 22 | 0 | 30 | 50 | 87.7 | 90.2 |
| 10% Pt/C | E | 0.05% | 32 | 0 | 30 | 90 | 94.6 | 94.6 |

3-Chloro-1H-pyrazol-4-amine hydrochloride (1a):

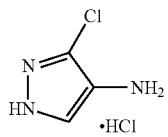

To a Hastelloy® C autoclave reactor was added 4-nitropyrazole (4.61 g, 40.8 mmol), ethanol (45 mL) and 31% hydrochloric acid (60 mL) (v/v 3:4), and palladium on alumina (5 weight percent, 0.240 g, 0.110 mmol). The reactor was assembled and stirred under a nitrogen atmosphere. The reaction temperature was adjusted to 30° C., and the mixture was sparged with nitrogen (2×) and then checked for pressure leaks using nitrogen. The reaction was then purged with hydrogen (720 kPa) to remove an excess nitrogen and then vented. Hydrogen was then added to a pressure of 720 kPa and the reaction was heated to 40° C. When the reaction was complete the vessel was purged with nitrogen (2×) and disassembled. The crude solution was then filtered using a glass fiber filter and assayed using an internal standard HPLC method (4.50 g, 75%): ¹H NMR (400 MHz, MeOD) δ 8.03; ¹³C NMR (400 MHz, MeOD) δ 110.91, 127.64, 134.80. The ratio of the title compound to 1H-pyrazole-4-amine hydrochloride (about 7:1) was determined by ¹H NMR.

Example 2

3-Chloro-1H-pyrazol-4-amine Hydrochloride (1a)

To a Hastelloy° C. autoclave reactor was added 4-nitropyrazole (4.50 g, 39.8 mmol), ethanol (45 mL) and 37% hydrochloric acid (60 mL) (v/v 3:4), and palladium on alumina (5 weight percent, 0.240 g, 0.110 mmol). The reactor was assembled and stirred under a nitrogen atmosphere. The reaction temperature was adjusted to 30° C., and the mixture was sparged with nitrogen (2×) and then checked for pressure leaks using nitrogen. The reaction was then purged with hydrogen (990 kPa) to remove an excess nitrogen and then vented. Hydrogen was then added to a pressure of 720 kPa and the reaction was heated to 40° C. When the reaction was complete the vessel was purged with nitrogen (2×) and disassembled. The crude solution was then filtered using a glass fiber filter and assayed using an internal standard HPLC method (4.71 g, 77%). The ratio of the title compound to 1H-pyrazole-4-amine hydrochloride (10:1) was determined by ¹H NMR.

Example 3

3-Chloro-1H-pyrazol-4-amine Hydrochloride (1a)

To a glass reactor (4 L) was added 4-nitropyrazole (76.3 g, 0.66 mol), palladium on alumina (5 weight percent, 44.4 g, 19.9 mmol), and 31% hydrochloric acid (1035 g). The reactor temperature was adjusted to 30° C. The reactor headspace was purged with nitrogen, then hydrogen gas (without agitation). The agitation blade speed was set to 300 RPM, and then hydrogen gas (100 kPa) was bubbled (subsurface) through the reactor at a flow rate less than 100 mL/min. Upon reaction completion, the reactor was purged with nitrogen. The crude solution was then filtered using a glass fiber filter and assayed using an internal standard HPLC method (88.4 g, 87%). The ratio of the title compound to 1H-pyrazole-4-amine hydrochloride (12:1) was determined by ¹H NMR.

Example: 4

3-Chloro-1H-pyrazol-4-amine Hydrochloride (1a)

To a glass reactor (4 L) was added 4-nitropyrazole (76.3 g, 0.66 mol), palladium on alumina (5 weight percent, 44.4 g, 19.9 mmol), and 37% hydrochloric acid (1035 g). The reactor temperature was adjusted to 30° C. The reactor headspace was purged with nitrogen, then hydrogen gas (without agitation). The agitation blade speed was set to 300 RPM, and then hydrogen gas (100 kPa) was bubbled (subsurface) through the reactor at a flow rate less than 100 mL/min. Upon reaction completion, the reactor was purged with nitrogen. The crude solution was then filtered using a glass fiber filter and assayed using an internal standard HPLC method (97.6 g, 96%). The ratio of the title compound to 1H-pyrazole-4-amine hydrochloride (32:1) was determined by $^1$H NMR.

Example 5

3-Chloro-1H-pyrazol-4-amine Hydrochloride (1a)

To a glass reactor (4 L) was added 4-nitropyrazole (76.3 g, 0.66 mol), palladium on alumina (5 weight percent, 44.4 g, 19.9 mmol), and 37% hydrochloric acid (1035 g). The reactor temperature was adjusted to 40° C. The reactor headspace was purged with nitrogen, then hydrogen gas (without agitation). The agitation blade speed was set to 300 RPM, and then hydrogen gas (100 kPa) was bubbled (subsurface) through the reactor at a flow rate less than 100 mL/min. Upon reaction completion, the reactor was purged with nitrogen. The crude solution was then filtered using a glass fiber filter and assayed using an internal standard HPLC method (96.6 g, 95%). The ratio of the title compound to 1H-pyrazole-4-amine hydrochloride (49:1) was determined by $^1$H NMR.

Example 6

3-Chloro-1H-pyrazol-4-amine Hydrochloride (1a)

To a glass reactor (150 mL) was added 4-nitropyrazole (9.82 g, 85.3 mmol), palladium on alumina (5 weight percent, 5.81 g, 2.5 mmol), and 37% hydrochloric acid (135.6 g). The reactor temperature was adjusted to 30° C. The agitation was started and the reactor was purged with nitrogen, then hydrogen gas. Hydrogen gas (about 240 kPa) was bubbled (subsurface) through the reactor at a flow rate less than 50 mL/min Upon reaction completion, the reactor was purged with nitrogen. The crude reaction mixture was assayed using an internal standard HPLC method. The mole ratio of the title compound to 1H-pyrazole-4-amine hydrochloride (25:1) was determined by $^1$H NMR.

Example 7

3-Chloro-1H-pyrazol-4-amine Hydrochloride (1a)

To a glass reactor (4 L) was added 4-nitropyrazole (154 g, 1.33 mol), palladium on alumina (4.77 weight percent, 29.6 g, 13 3 mmol), isopropanol (138 g), and about 37% hydrochloric acid (1896 g) (v/v 1:9). The reactor temperature was adjusted to 30° C. The reactor headspace was purged with nitrogen, then hydrogen gas (without agitation). The agitation blade speed was set to 400 RPM, and then hydrogen gas (about 100 kPa) was bubbled (subsurface) through the reactor at a flow rate less than 100 mL/min. Upon reaction completion, the reactor was purged with nitrogen. The crude solution was then filtered using a glass fiber filter and assayed using an internal standard HPLC method (196 g, 95%). The ratio of the title compound to 1H-pyrazole-4-amine hydrochloride (24:1) was determined by $^1$H NMR.

Example 8

3-Chloro-1H-pyrazol-4-amine Hydrochloride (1a)

To a glass-lined Hastelloy® C autoclave reactor was added 4-nitropyrazole (7.17 g, 61.9 mmol), isopropanol (8.15 mL), and about 37% hydrochloric acid (73.5 mL) (v/v 1:9), and platinum on carbon (5 weight percent, 1.35 g, 0.54 mol %). The reactor was sealed and the vessel was purged with nitrogen (about 1000 kPa) and vented (2×). The vessel was vented and then purged with hydrogen gas (about 800 kPa) and then pressurized to about 720 kPa with hydrogen gas. The reaction was heated to 30° C., and the agitation was set to 800 RPM. The hydrogen uptake rate was monitored and the reaction was continued until the hydrogen uptake ceased. The vessel was vented and purged with nitrogen (2×). The reactor was opened, and the product mixture was collected. The reaction mixture was assayed using an internal standard HPLC method (9.24 g, 97%). The ratio of the title compound to 1H-pyrazole-4-amine hydrochloride (24:1) was determined by $^1$H NMR.

COMPARATIVE EXAMPLES

Example CE-1

Synthesis of 3-chloro-1H-pyrazol-4-amine Hydrochloride (1a) Using Dahlbom et al. Method Example CE-1 is a comparative example wherein 4-nitropyrazole is halogenated and reduced with the Dahlbom et al. conditions. Treatment of 4-nitropyrazole with about 15% (5 M) hydrochloric acid in ethanol at a v/v ratio of ethanol to hydrochloric acid of about 4:1, afforded the halogenated product 3-chloro-1H-pyrazol-4-amine hydrochloride (1a) with a 1.6 times to 9.8 times less or 160% to 980% lower selectivity to the undesired non-halogenated product 1H-pyrazol-4-amine hydrochloride, than the selectivity obtained using the conditions of the present disclosure.

The Dahlbom report does not disclose the temperature at which this process is conducted, nor does it report the catalyst loading of palladium on alumina The following reaction was conducted at room temperature with a catalyst loading of palladium on alumina of 0.3 mol percent.

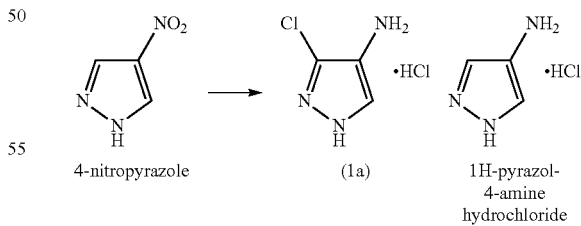

A Parr bottle (500 mL) was charged with 4-nitropyrazole (3.00 g, 26.5 mmol), palladium on alumina (5 weight percent, 0.150 g, 0.0705 mmol), about 15% (5 M) hydrochloric acid (12 mL), and ethanol (50 mL). The mixture was purged with nitrogen (3×), and hydrogen (3×). The reaction was agitated under 3-3.5 atmospheres (about 300 to about 350 kPa) hydrogen gas for 2 hours. The reaction mixture was filtered, and the filtrates were concentrated to afford the crude product as a yellow solid (3.1 g). $^1$H NMR indicated that the crude product contained 4-nitropyrazole, 3-chloro-1H-pyrazol-4-amine hydrochloride, and 1H-pyrazole-4-amine hydrochloride in a ratio of 1.3:1:0.2. The combined yield of 3-chloro-1H-pyrazol-4-amine hydrochloride and 1H-pyrazole-4-amine hydrochloride was determined to be about 48%. The ratio of 3-chloro-1H-pyrazol-4-amine hydrochloride to 1H-pyrazole-4-amine hydrochloride was determined by $^1$H NMR to be about 5:1.

This example shows that by utilizing the conditions reported by Dahlbom et al., that a poor selectivity of halogenated product 3-chloro-1H-pyrazol-4-amine hydrochloride (1a)

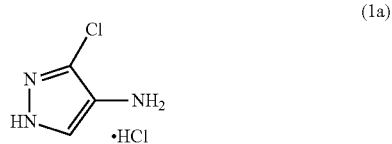

to non-halogenated by-product 1H-pyrazol-4-amine hydrochloride

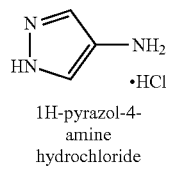

1H-pyrazol-4-amine hydrochloride of about 5:1 was observed.

In their report, Dahlbom et al. do not recognize a selectivity problem associated with halogenating and reducing 4-nitropyrazole with their reported conditions. Consequently, they do not address what, if any, reaction variables might be optimized to improve the poor selectivity.

Example CE-2

Synthesis of 3-chloro-1H-pyrazol-4-amine Hydrochloride (1a) Using Diluted Hydrochloric Acid such as Taught by Ramsden et al., Optionally in the Presence of Ethanol Example CE-2 is a further comparative example wherein 4-nitropyrazole is halogenated and reduced with similar conditions to those reported by Ramsden et al. Treatment of 4-nitropyrazole with about 19% (about 6 M) hydrochloric acid in ethanol at a v/v ratio of ethanol to hydrochloric acid of 5:2, afforded the desired halogenated product 3-chloro-1H-pyrazol-4-amine hydrochloride (1a) with 2.6 times to 16 times less or 260% to 1600% lower selectivity to the undesired non-halogenated product 1H-pyrazol-4-amine hydrochloride, than the selectivity obtained using the conditions of the present disclosure.

The Ramsden report does not disclose the weight percent of palladium on alumina or the type of reaction vessel used. The following reaction was conducted in HasteHoy® C autoclave reactor with a weight percent of palladium on alumina of 5 weight percent.

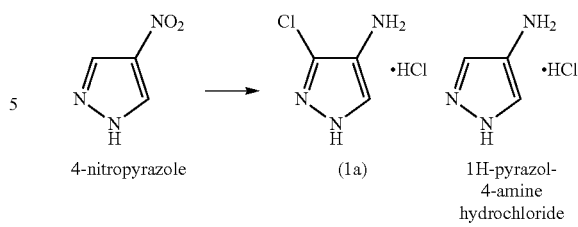

To a Hastelloy® C autoclave reactor was added 4-nitropyrazole (4.50 g, 39.8 mmol), ethanol, about 19% (about 6 M) hydrochloric acid, and palladium on alumina (5 weight percent, 0.240 g, 0.110 mmol). The reactor was assembled and stirred under a nitrogen atmosphere. The reaction temperature was adjusted to 30° C., and the mixture was sparged with nitrogen (2×) and then checked for pressure leaks using nitrogen. The reaction was then purged with hydrogen (about 990 kPa) to remove an excess nitrogen and then vented. Hydrogen was then added to a pressure of about 720 kPa and the reaction was heated to 40° C. When the reaction was complete the vessel was purged with nitrogen (2×) and disassembled. The crude solution was then filtered using a glass fiber filter and assayed using an internal standard HPLC method (3.60 g, 59%, in pot). The ratio of the title compound to 1H-pyrazole-4-amine hydrochloride was determined by $^1$H NMR to be about 3:1.

This example shows that by utilizing similar conditions reported by Ramsden et al., that a poor selectivity of halogenated product 3-chloro-1H-pyrazol-4-amine hydrochloride (1a) to non-halogenated by-product 1H-pyrazol-4-amine hydrochloride of about 3:1 was observed.

In their report, Ramsden et al. do not recognize a selectivity problem associated with halogenating and reducing 4-nitropyrazole with their reported conditions. Consequently, they do not address what, if any, reaction variables might be optimized to improve the poor selectivity.

Example CE-3

Synthesis of 3-chloro-1H-pyrazol-4-amine Hydrochloride (1a)

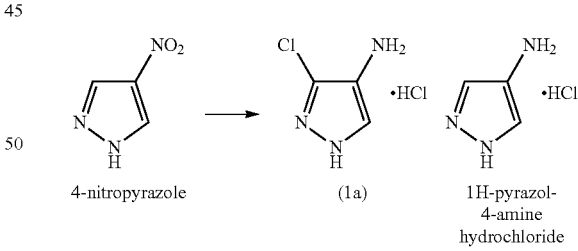

Example CE-3 are further comparative examples wherein 4-nitropyrazole is halogenated and reduced with dilute hydrochloric acid (less than 31%). Treatment of 4-nitropyrazole with diluted hydrochloric acid (less than 31%), optionally in the presence of an additional alcoholic solvent at a v/v ratio of alcoholic solvent to hydrochloric acid of about 1:6 to about 3:4, afforded the desired halogenated product 3-chloro-1H-pyrazol-4-amine hydrochloride (1a) with at most 1.1 times to 7 times less or 110% to 700% lower selectivity to the undesired non-halogenated product 1H-pyrazol-4-amine hydrochloride, than the selectivity obtained using the conditions of the present disclosure.

Procedure A

To a Hastelloy® C autoclave reactor was added 4-nitropyrazole (4.50 g, 39.8 mmol), ethanol, hydrochloric acid, and palladium on alumina (5 weight percent, 0.240 g, 0.110 mmol). The reactor was assembled and stirred under a nitrogen atmosphere. The reaction temperature was adjusted to 30° C., and the mixture was sparged with nitrogen (2×) and then checked for pressure leaks using nitrogen. The reaction was then purged with hydrogen (about 990 kPa) to remove an excess nitrogen and then vented. Hydrogen was then added to the stated pressure and the reaction was heated to 40° C. When the reaction was complete the vessel was purged with nitrogen (2×) and disassembled. The crude solution was then filtered using a glass fiber filter and assayed using an internal standard HPLC method. The ratio of the title compound to 1H-pyrazole-4-amine hydrochloride was determined by $^1$H NMR. See Table CE-3 DATA.

Procedure B

To a glass reactor (4 L) was added 4-nitropyrazole (76.3 g, 0.66 mol), palladium on alumina (5 weight percent, 44.4 g, 19.9 mmol), and hydrochloric acid (18% or 5.7 M, 1035 g). The reactor temperature was adjusted to 30° C. The reactor headspace was purged with nitrogen, then hydrogen gas (without agitation). The agitation blade speed was set to 300 RPM, and then hydrogen gas (about 100 kPa) was bubbled (subsurface) through the reactor at a flow rate less than 100 mL/min Upon reaction completion, the reactor was purged with nitrogen. The crude solution was then filtered using a glass fiber filter and assayed using an internal standard HPLC method. The ratio of the title compound to 1H-pyrazole-4-amine hydrochloride was determined by $^1$H NMR. See TABLE CE-3 DATA.

TABLE

CE-3 DATA

| Entry | Procedure | HCl Concentration | Ethanol to HCl ratio (v/v) | Hydrogen (kPa) | 1a yield (in pot %) | 1a:1H-pyrazole-4-amine hydrochloride molar ratio |
|---|---|---|---|---|---|---|
| 1 | A | 6M (19%) | 2:3 | 720 | 69 | 5:1 |
| 2 | A | 6M (19%) | 1:6 | 720 | 68 | 7:1 |
| 3 | A | 9M (28%) | 3:4 | 100 | 74 | 6:1 |
| 4 | B | 5.7M (18%) | — | 100 | 81 | 4:1 |

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:

1. A process for the preparation of 3-chloro-1H-pyrazol-4-amine hydrochloride (1a)

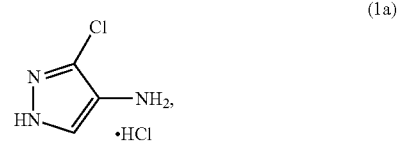

(1a)

comprising halogenating and reducing 4-nitropyrazole

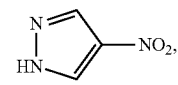

with
(a) about 17% to about 40% hydrochloric acid,
(b) hydrogen gas at pressures of about 100 kPa to about 800 kPa, and
(c) a transition metal catalyst selected from the group consisting of palladium on alumina (Pd/Al$_2$O$_3$), palladium on carbon (Pd/C), platinum on carbon (Pt/C), and mixtures thereof,
at temperatures of about 20° C. to about 60° C., optionally in the presence of an alcoholic solvent at a v/v ratio of alcoholic solvent to hydrochloric acid of about 1:99 to about 3:4.

2. The process according to claim 1, wherein the transition metal catalyst is palladium on alumina.

3. The process according to claim 1, wherein the transition metal catalyst is palladium on carbon.

4. The process according to claim 1, comprising about 36% to about 38% hydrochloric acid.

5. The process according to claim 1, wherein the temperature is about 20° C. to about 40° C.

6. The process according to claim 1, wherein the v/v ratio of alcoholic solvent to hydrochloric acid is about 1:9 to about 3:4.

7. The process according to claim 1, wherein the transition metal catalyst is platinum on carbon.

8. The process according to claim 7, wherein the hydrochloric acid is about 17% to about 22% v/v.

9. The process according to claim 8, wherein the v/v ratio of alcoholic solvent to hydrochloric acid is about 1:9 to about 3:4.

10. The process according to claim 9, wherein the v/v ratio of alcoholic solvent to hydrochloric acid is about 1:9.

11. The process according to claim 7, wherein the hydrochloric acid is about 17% to about 27% v/v.

12. The process according to claim 11, wherein the v/v ratio of alcoholic solvent to hydrochloric acid is about 1:9 to about 3:4.

13. The process according to claim 12, wherein the v/v ratio of alcoholic solvent to hydrochloric acid is about 1:9.

14. A process according to claim 1, further comprising free-basing 3-chloro-1H-pyrazol-4-amine hydrochloride (1a)

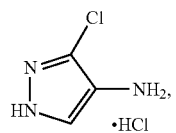

(1a)

with a base to yield 3-chloro-1H-pyrazol-4-amine (1)

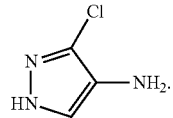

(1)

15. A process according to claim 1, wherein the palladium on alumina has a metal to solid support weight percentage of about 1 weight percent to about 10 weight percent.

16. A process according to claim 1, wherein the platinum on carbon has a metal to solid support weight percentage of about 1 weight percent to about 10 weight percent.

17. The process according to claim 1, wherein the alcoholic solvent is ethanol.

18. The process according to claim 1, wherein the alcoholic solvent is isopropanol.

19. The process according to claim 1, wherein the process is performed in a glass-lined reactor.

* * * * *